United States Patent
Laboureau et al.

(10) Patent No.: US 9,687,434 B2
(45) Date of Patent: Jun. 27, 2017

(54) COSMETIC USE OF STEVIOL, OF A STEVIOL GLYCOSIDE DERIVATIVE OR OF ONE OF THEIR ISOMERS TO STIMULATE, RESTORE OR REGULATE THE METABOLISM OF THE CELLS OF THE SKIN AND SEMIMUCUS MEMBRANES

(71) Applicant: L'OREAL, Paris (FR)

(72) Inventors: Julien Laboureau, Issy les Moulineaux (FR); Myrian Kauffmann, Ivry sur Seine (FR); Yann Mahe, Sainte Genevieve des Bois (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/368,212

(22) PCT Filed: Dec. 21, 2012

(86) PCT No.: PCT/IB2012/057614
§ 371 (c)(1),
(2) Date: Jun. 23, 2014

(87) PCT Pub. No.: WO2013/093881
PCT Pub. Date: Jun. 27, 2013

(65) Prior Publication Data
US 2015/0011493 A1   Jan. 8, 2015

Related U.S. Application Data

(60) Provisional application No. 61/585,086, filed on Jan. 10, 2012.

(30) Foreign Application Priority Data

Dec. 23, 2011   (FR) ..................... 11 62394

(51) Int. Cl.
| | |
|---|---|
| A61K 8/60 | (2006.01) |
| A61Q 19/00 | (2006.01) |
| A61Q 19/08 | (2006.01) |
| A61K 8/97 | (2017.01) |
| A61K 8/365 | (2006.01) |
| A61K 8/36 | (2006.01) |
| A61Q 1/12 | (2006.01) |

(52) U.S. Cl.
CPC ............... *A61K 8/602* (2013.01); *A61K 8/36* (2013.01); *A61K 8/365* (2013.01); *A61K 8/97* (2013.01); *A61Q 1/12* (2013.01); *A61Q 19/00* (2013.01); *A61Q 19/08* (2013.01); *A61K 2800/74* (2013.01); *A61K 2800/88* (2013.01); *A61K 2800/91* (2013.01); *A61K 2800/92* (2013.01)

(58) Field of Classification Search
CPC .......... A61K 8/602; A61K 8/97; A61Q 19/00; A61Q 19/08
See application file for complete search history.

(56) References Cited

U.S. PATENT DOCUMENTS

2005/0129618 A1   6/2005   Ashida et al.

FOREIGN PATENT DOCUMENTS

| CN | 101062077 | 10/2007 | |
|---|---|---|---|
| EP | 1 457 780 | 9/2004 | |
| JP | 7 17847 | 1/1995 | |
| JP | 07017847 | 1/1995 | |
| JP | 2008037758 A * | 2/2008 | ............... A61K 8/60 |
| JP | 2011126795 A * | 6/2011 | ........... A61K 31/704 |
| WO | 2009/071277 | 6/2009 | |

OTHER PUBLICATIONS

International Stevia Council web site, http://www.internationalsteviacouncil.org/index.php?id=152, accessed online on Dec. 10, 2015.*
Definition of prevent, Oxford English Dictionary Online, http://dictionary.oed.com/, accessed online Mar. 27, 2010, especially definition 9a. at p. 2.*
English machine translation of JP 2011126795 A, AIPN online translation, https://dossier1.j-platpat.inpit.go.jp/, accessed online on Dec. 10, 2015.*
Entry for wrinkles, MedlinePlus Medical Encyclopedia, http://www.nlm.nih.gov/medlineplus/ency/article/003252.htm, accessed online on Sep. 21, 2011.*
Entry for wrinkles, MayoClinic.com, http://www.mayoclinic.com/health/wrinkles/DS00890, accessed online on Sep. 21, 2011.*
English machine translation of JP 2008037758 A, AIPN online translation, https://dossier1.j-platpat.inpit.go.jp/, accessed online on Dec. 10, 2015.*
Hirano, et al., "Skin-lightening, -conditioning, and -antiaging beverage or foods containing pearl", Chemical Abstracts Service, Total 1 Page, (Oct. 28, 2003) XP-002288259.
Abudula, R. et al., "Rebaudioside a Potently Stimulates Insulin Secretion From Isolated Mouse, Islets: Studies on the Dose-, Glucose-, and Calcium-Dependency", Metabolism, vol. 53, No. 10, pp. 1378-1381, (Oct. 2004).
International Search Report and Written Opinion Issued May 2, 2013 in PCT/IB12/057614 Filed Dec. 21, 2012.
French Search Report and French Written Opinion Issued Nov. 16, 2012 in French Application No. 1162394 Filed Dec. 23, 2011 (with English translation).
Office Action as received in the corresponding European Patent Application No. 12 824 722.8-1458 dated Jul. 22, 2016.
Office Action as received in the corresponding Chinese Patent Application No. 201280070622.0 dated Apr. 25, 2016 w/Partial English Translation.
Database GNPD No. 1063215, Feb. 2009, Mintel, 5 pages, www.gnpd.com.
Database GNPD No. 1583388, Jun. 2011, Mintel, www.gnpd.com.
Database GNPD No. 1222747, Nov. 2009, 6 pages, Mintel, www.gnpd.com.

* cited by examiner

*Primary Examiner* — Jonathan S Lau
(74) *Attorney, Agent, or Firm* — Oblon, McClelland, Maier & Neustadt, L.L.P.

(57) ABSTRACT

The present invention relates to the cosmetic use by external topical route of steviol, of a steviol glycoside derivative or of one of their isomers to stimulate, restore or regulate the metabolism of the cells of the skin.

18 Claims, No Drawings

COSMETIC USE OF STEVIOL, OF A STEVIOL GLYCOSIDE DERIVATIVE OR OF ONE OF THEIR ISOMERS TO STIMULATE, RESTORE OR REGULATE THE METABOLISM OF THE CELLS OF THE SKIN AND SEMIMUCUS MEMBRANES

CROSS REFERENCE TO RELATED APPLICATIONS

The present application is a 35 U.S.C. §371 national stage patent application of International patent application PCT/IB2012/057614, filed on Dec. 21, 2012, published as WO/2013/093881 on Jun. 27, 2013, the text of which is incorporated by reference, and claims the benefit of the filing date of French application no. 1162394, filed on Dec. 23, 2011, and U.S. provisional application No. 61/585,086, filed on Jan. 10, 2012, the text of each of which is also incorporated by reference.

The invention relates to the field of cosmetic active agents and more particularly active agents devoted to acting with regard to aging of the skin.

Human skin consists of several compartments, three of which cover the whole of the body, namely a superficial compartment, which is the epidermis, the dermis and a deep compartment, which is the hypodermis. The epidermis is a keratinized stratified pavement epithelium. It is composed mainly of keratinocytes but also of other cells and rests on a basal membrane which separates it from the dermis. The dermis is a connective tissue. Its architecture results from the arrangement and the interactions between the constituents of the extracellular matrix and the fibroblasts, which carry out the synthesis thereof and the degradation thereof. It makes up the main bulk of skin. The dermis is subdivided into two layers, the papillary layer and the reticular layer. The dermis is composed of collagen fibers and elastin fibers, and also of glycosaminoglycans and proteoglycans. These different structures form a complex network which plays a key role in the biomechanical properties of the skin. Finally, the hypodermis, the deepest compartment and generally the thickest compartment of the skin, invaginates into the dermis and is attached to the overlying dermis via collagen and elastin fibers. It is essentially composed of a type of cells which are specialized in the accumulation and storage of fats, the adipocytes. In the region where the tegumentary covering is not keratinized, the epidermis is referred to as mucus membrane. This epithelium also comprises fibroblasts within a dermal matrix.

The skin tissue also comprises appendages, such as sweat glands, pilosebaceous follicles, body hair, head hair and nails.

During chronological and/or photoinduced aging, the skin and more particularly the dermis is subjected to numerous modifications and types of damage. In particular, numerous detrimental changes in the skin, resulting from a dysfunctioning of its homeostasis and in particular from a dysfunctioning of the metabolism of the fibroblasts, occur. At the cell level, aging is reflected by a detrimental change in the physiology or metabolism of the main cell types of the dermis, in particular fibroblasts, and of the epidermis, such as the keratinocytes. At the tissue level, ageing is expressed by disruption of the architecture of the epidermis, of the dermal-epidermal junction of the dermis and also of the blood irrigation and innervation systems, and a slowing down of various types of metabolism, such as those involved in the equilibrium of the barrier function.

This deregulation of the cell metabolism of the cells of the skin, in particular the fibroblasts, can be reflected by a detrimental change in the microrelief, the appearance of wrinkles and fine lines, a detrimental change in the mechanical properties of the skin, with a decrease in firmness and elasticity, or a detrimental change in the radiance of the complexion of the skin and its apparent age. Histologically, a flattening of the dermal-epidermal junction and a decrease in the thickness of the dermis are observed.

Furthermore, the detrimental change in the mechanical properties of the skin can be accentuated by various secondary factors, such as the consequence of various physiological disorders, such as, for example, metabolic diseases, a hypo- or hypersecretion of hormones, a vitamin deficiency or a disorder of gene expression, environmental attacks, such as pollution or radiation, extrinsic factors, such as tobacco, inflammation, variations in the organisation, in the density of the hypodermis, following a modification in body mass, pregnancy, a state of obesity, cellulitis, medical treatments, for example with topical corticosteroids, or else disruption of the constituents of the extracellular matrix resulting, for example, from stretch marks, scars or bedsores.

In addition, at the menopause, the dermis can be detrimentally affected by a decrease in its dermal thickness and an accentuation in the fine surface wrinkles and fine surface lines may be observed. The skin then exhibits a rough aspect to the touch and reduced suppleness.

The importance is understood, from the above, of being able to have available products capable of effectively acting on the cells of young or elderly skin in order to limit the detrimental change in the ways they function and their aging, in particular with regard to fibroblasts, in order to prevent, reduce and/or treat signs of aging of the skin.

It is an object of the present invention to satisfy these needs.

Unexpectedly, the inventors have observed that a steviol, a steviol glycoside derivative or one of their isomers proves to be particularly advantageous for preventing or treating disorders related to skin aging, whether chronobiological or photobiological.

This is because, as emerges from the examples below, the inventors have found, unexpectedly, that a steviol, a steviol glycoside derivative or one of their isomers effectively brings about contraction of the fibroblasts. This contraction of the fibroblasts results in a densification of the dermis which, for obvious reasons, makes it possible to prevent and/or treat the deep wrinkles and the loss in firmness of the skin, to control the homeostasis of the skin and to stimulate its regeneration in order to combat the appearance of signs of aging of the skin, whether chronological and/or photoinduced.

Thus, according to a first of its aspects, a subject matter of the invention is the use, in particular cosmetic use, of steviol, of a steviol glycoside derivative or of one of their isomers to stimulate, restore or regulate the metabolism of the cells of the skin and semimucus membranes, preferably of the cells of the dermis and more particularly of the fibroblasts.

The term "metabolism" is intended to denote, within the meaning of the present invention, the group of molecular and energy transformations which take place in a living cell and which contribute to its homeostasis, that is to say its maintenance of biological activity and of physiological balance.

According to another of its aspects, a subject matter of the invention is the use, in particular cosmetic use, of steviol, of a steviol glycoside derivative or of one of their isomers to prevent and/or treat signs of aging of the skin and semimucus membranes.

Within the meaning of the present invention, the term "mucus membrane" denotes in particular the lips.

Within the meaning of the invention, the term "signs of aging of the skin" is understood to mean any modification to the external appearance of the skin due to aging, whether chronobiological and/or photoinduced, such as, for example, wrinkles and fine lines, withered skin, flabby skin, thinned skin, lack of elasticity and/or tonicity of the skin or lack of density and/or firmness of the skin, but also any internal modification to the skin not automatically reflected by a modified external appearance, such as, for example, any internal damage to the skin resulting from exposure to ultraviolet radiation.

To the knowledge of the inventors, the antiaging activity of steviol, of a steviol glycoside derivative or of one of their isomers has never to date been described.

Admittedly, these compounds have already been proposed as sweetener (EP 1 856 967) or as promoter of the dissolution of compounds which are insoluble or only sparingly soluble in an aqueous medium (WO 2009/126950). The scientific literature furthermore suggests that rebaudioside A might be a molecule of interest in regulating glycemia or the metabolism of the cells of the pancreas and treating diabetes (Abudula et al., Metabolism, 2004, 53, 1378; WO 02/060419), in improving cognitive functions (WO 2009/071277) or in treating cardiovascular diseases (WO 2008/134828).

Likewise, some authors furthermore describe their use in particular for treating greasy skin or acne by regulating the metabolism of the sebocytes (U.S. Pat. No. 5,110,801) or alternatively for combating inflammatory phenomena (allergy, dermatitis) (JP-08325156-A). Finally, WO 07/094,312 proposes the use of steviosides to promote the penetration of vitamin C into cells.

However, until now, no direct effect on cells of the dermis (fibroblasts) nor effect on the semimucus membranes accessible by the topical route, other than the production of sweet sensations, had been demonstrated.

Another subject matter of the invention is the use, in particular cosmetic use, of steviol, of a steviol glycoside derivative or of one of their isomers to prevent, reduce and/or treat wrinkles, fine lines or a detrimental change in microrelief.

A further subject matter of the invention is the use, in particular cosmetic use, of steviol, of a steviol glycoside derivative or of one of their isomers to strengthen the mechanical properties of the skin and semimucus membranes, in particular to combat withered, flabby, distended, sunken and/or thinned skin, and/or to strengthen and/or restore the elasticity or firmness of the skin.

A further subject matter of the invention is the use, in particular cosmetic use, of steviol, of a steviol glycoside derivative or of one of their isomers to prevent a detrimental change in and/or to maintain the homeostasis of the skin and semimucus membranes.

A further subject matter of the invention is the use, in particular cosmetic use, of steviol, of a steviol glycoside derivative or of one of their isomers to prevent and/or treat skin conditions related to the menopause.

Within the meaning of the present invention, the term "to prevent" is understood to mean the fact of reducing, at least in part, the risk of the appearance of a given phenomenon, i.e., in the presence invention, detrimental changes in the metabolism of elderly skin cells and/or signs of aging of the skin, in particular those defined above.

According to another of its aspects, the invention is targeted at steviol, a steviol glycoside derivative or one of their isomers as agent, in particular cosmetic or dermatological agent, for stimulating, restoring or regulating the metabolism of cells of the skin and semimucus membranes.

It is also targeted at steviol, a steviol glycoside derivative or one of their isomers, to prevent and/or treat signs of aging of the skin or semimucus membranes.

It is also targeted at steviol, a steviol glycoside derivative or one of their isomers as agent, in particular cosmetic or dermatological agent, for preventing, reducing and/or treating wrinkles, fine lines or a detrimental change in microrelief.

It is also targeted at steviol, a steviol glycoside derivative or one of their isomers as agent, in particular cosmetic or dermatological agent, for strengthening the mechanical properties of the skin and semimucus membranes, in particular for combating withered, flabby, distended, sunken and/or thinned skin, and/or for strengthening and/or restoring the elasticity or firmness of the skin.

It is also targeted at steviol, a steviol glycoside derivative or one of their isomers as agent, in particular cosmetic or dermatological agent, for preventing a detrimental change in and/or maintaining the homeostasis of the skin or semimucus membranes.

It is also targeted at steviol, a steviol glycoside derivative or one of their isomers as agent, in particular cosmetic or dermatological agent, for preventing and/or treating skin conditions related to the menopause.

According to yet another of its aspects, the present invention is targeted at a cosmetic or dermatological composition comprising at least an effective amount of steviol, of a steviol glycoside derivative or of one of their isomers, in particular as defined below, in combination with at least one additional active agent chosen from a sweetener, an amino acid, a peptide, an agonist of extracellular calcium receptors, an agonist of calcium channels, an antiwrinkle active agent, an antiaging active agent, a moisturizing agent, an antioxidant, a photoprotective agent and their mixtures.

According to yet another of its aspects, the present invention is targeted at a kit comprising at least one container containing a composition comprising steviol, a steviol glycoside derivative or one of their isomers and at least one device arranged in order to make possible the administration of said composition to an individual, and/or to increase the effectiveness of said composition for an individual, and/or to promote the topical penetration of said composition for an individual.

As emerges from what follows, this device can be adjusted to an intracutaneous injection, such as a syringe, an implant or microneedles. It can also be an ultrasound or iontophoresis device, or else a light or thermal device.

According to yet another of its aspects, the present invention is targeted at a method, in particular a cosmetic method, for stimulating, restoring or regulating the metabolism of cells of the skin or semimucus membranes, comprising at least one stage of administration, to an individual having need thereof, of at least an effective amount of steviol, of a steviol glycoside derivative or of one of their isomers.

According to yet another of its aspects, the present invention is targeted at a method, in particular a cosmetic method, for preventing and/or treating signs of aging of the skin or semimucus membranes, comprising at least one stage of administration, to an individual having need thereof, of at least an effective amount of steviol, of a steviol glycoside derivative or of one of their isomers.

Preferably, indications subject-matter of the uses according to the invention are indications not involving the production and/or release of stem cell factor (SCF).

As emerges from what follows, the steviol, a steviol glycoside derivative or one of their isomers can be administered by the external topical route, by the intracutaneous, intradermal or subcutaneous route or by the oral route and preferably by the external topical route.

Steviol

The present invention relates to the use of an active agent chosen from a steviol, a steviol glycoside derivative or one of their isomers.

Steviol is represented by the formula (I):

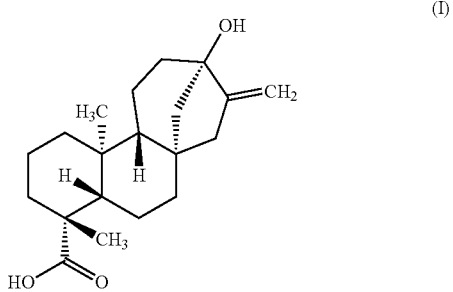

(I)

Steviol is the common precursor of the steviol glycosides.

The term "precursor" is understood to mean, within the meaning of the present invention, any compound participating in a reaction which produces one or more other compounds.

The term "steviol glycoside derivative" is understood to mean any compound represented by the formula (II):

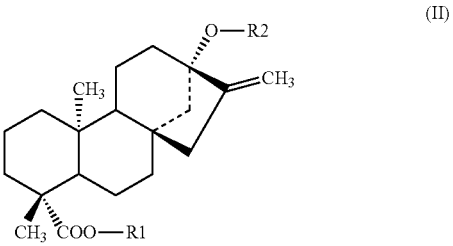

(II)

in which R1 and R2, respectively positioned on carbons $C_{19}$ and $C_{13}$ of the formula (II), represent, independently of one another, a hydrogen atom or a cyclized or noncyclized, linear or branched, sugar residue.

Preferably, R1 and R2 are other than hydrogen.

In particular, R1 and R2, which are identical or different and preferably different, represent a sugar residue composed of one or more glucose and/or rhamnose entities.

Mention may in particular be made, by way of illustration and without implied limitation of these sugar residues, of the groups consisting of:
  just one sugar entity, in particular glucose entity, referred to as Glu,
  a sequence of two sugars, such as a diholoside, for example a sequence of two glucose entities, or
  a sequence of three sugar units, such as a linear or branched and preferably branched triholoside, for example a branched radical formed of three glucose units and a branched radical formed of a glucose entity substituted by a glucose entity and a rhamnose entity.

According to a specific alternative form, R1 represents a glucose entity.

According to a more preferred alternative form, R1 represents a glucose unit and R2 represents a branched triholoside.

The detailed structures of some steviol glycoside derivatives of formula (II) suitable for the invention are reported in table I below.

|  | R1 | R2 |
| --- | --- | --- |
| stevioside | Glu | Glu-Glu |
| rebaudioside A | Glu | Glu-Glu<br>\|<br>Glu |
| rebaudioside C | Glu | Glu-Rha<br>\|<br>Glu |
| dulcoside A | Glu | Glu-Rha |
| rubusoside | Glu | Glu |

Thus, a steviol glycoside derivative according to the invention can be chosen from stevioside, rebaudioside A, rebaudioside C (or dulcoside B), dulcoside A, rebaudioside B, rebaudioside D, rebaudioside E, rebaudioside F, steviolbioside, rubusoside, and their mixtures.

More preferably, a steviol glycoside derivative according to the invention is chosen from stevioside, rebaudioside A, rebaudioside C (or dulcoside B), dulcoside A, and their mixtures.

More preferably still, a steviol glycoside derivative according to the invention is rebaudioside A.

The term "isomer" is intended to denote, within the meaning of the present invention, at least two molecules having the same empirical formula but having different semi-expanded formulae or expanded formulae.

Preferably, isomers according to the invention are stereoisomers, in particular enantiomers, diastereomers, and mixtures thereof, including racemic mixtures.

Mention may in particular be made, as isomer according to the invention, of isosteviol, represented by the formula (III) below:

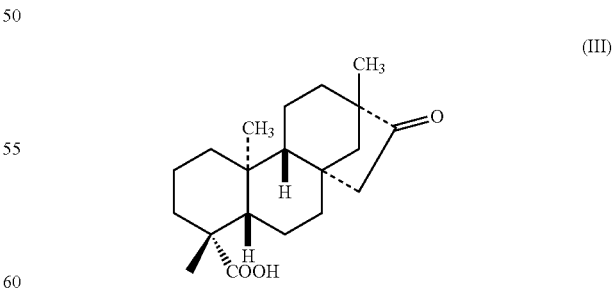

(III)

The present invention naturally employs an effective amount of steviol, steviol glycoside derivative or isomers of these, so as to obtain the desired effect. This effective amount can vary with regard to various parameters which are in particular the indication targeted, the characteristics of the individual treated, the pharmaceutical dosage formulation adopted, the nature of the formulation excipients or the presence of additional active agent(s).

Within the meaning of the present invention, the term "effective amount" is understood to mean a sufficient and necessary amount of a given active agent to exert the desired effect, namely, in the present invention, to stimulate, restore or regulate the metabolism of cells of the skin, in particular fibroblasts, or to prevent, reduce and/or treat signs of aging of the skin.

Such an amount can be determined by any method known to a person skilled in the art, for example by means of in vitro, ex vivo or in vivo trials, such as clinical trials.

In order to give an order of magnitude, steviol, a steviol glycoside derivative or an isomer of these can be used in a composition in a proportion of from 0.01% to 50% by weight, preferably from 0.05% to 30% by weight, in particular from 0.1% to 10% by weight and more preferably from 0.5% to 5% by weight, with respect to the total weight of the composition.

According to a preferred embodiment, a main active agent according to the invention, that is to say steviol, a steviol glycoside derivative or one of their isomers, is employed in the form of an extract of at least one plant of the *Stevia* genus.

The use of the main active agent according to the invention in the form of an extract of a least one plant of the *Stevia* genus is particularly advantageous in that it makes it possible to provide a novel cosmetic active agent of natural origin and thus to meet an increasing demand from consumers in this direction.

The *Stevia* genus belongs to the family of the Asteraceae, which brings together from 150 to 200 species of shrubs or aromatic herbs, some of which comprise natural sweeteners. The *Stevia* plants are plants originating from the tropical regions of Latin America.

According to the invention, the extract of a plant from the *Stevia* genus can be chemically modified (it is then semisynthetic), but it is preferably a native extract.

An extract of a plant of the *Stevia* genus, within the meaning of the present invention, can be prepared from any plant material resulting from said plant or from its cells cultivated according to conventional methods or by biotechnology in vivo or resulting from culturing in vitro.

The term "cultivating in vivo" is understood to mean any cultivation of conventional type, that is to say in soil in the open air or in a greenhouse, or alternatively without soil.

The term "culturing in vitro" is understood to mean all the techniques known to those skilled in the art which make it possible to artificially obtain a plant or a plant part. The selection pressure imposed by the physicochemical conditions during the growth of plant cells in vitro makes it possible to obtain a standardized plant material which is available throughout the year, in contrast to plants cultivated in vivo.

An extract of a plant of the *Stevia* genus employed in the present invention can be obtained from any plant material resulting from this whole plant or from any part of this plant, such as, for example, the leaves, stems, flowers and flowering tops, seeds, buds and roots, undifferentiated cells or plant stem cells.

Preferably, an extract of a plant of the *Stevia* genus in accordance with the invention is obtained from the leaves.

More preferably still, an extract of a plant of the *Stevia* genus in accordance with the invention originates from a plant of the species *Stevia rebaudiana* (Bertoni), also known as *Eupatorium rebaudianum* or "sweet leaf".

Such a species is today cultivated in many countries and on other continents than Latin America, in particular in Singapore, Taiwan, Malaysia, South Korea, China, Israel or even Australia.

Preferably, an extract of a plant of the *Stevia* genus according to the present invention is a native extract.

Within the invention, the term "native" intends to mean an extract that is not modified after the extraction process, especially by fermentation or by chemical synthesis.

Preferably, an extract of a plant of the *Stevia* genus according to the present invention is not a fermented extract.

Preferably, an extract of a plant of the *Stevia* genus according to the present invention is employed in a composition in a proportion of from 0.00001% to 50% by weight, preferably from 0.0001% to 10% by weight and better still from 0.01% to 4% by weight, with respect to the total weight of said composition.

Steviols have already been provided commercially.

Mention may in particular be made, as rebaudioside A which can be used in the present invention, of the *Stevia* extract comprising 99% of rebaudioside A sold by Blue California under the name Good'n Sweet™ as well as the *Stevia* extract comprising 97% of rebaudioside A sold by Chengdu Wagott Pharmaceutical under the name ViaSweet™.

Also concerned may be the *Stevia* extract fermented by a yeast described in the document WO2003/035090.

The intrinsic properties of a main active agent according to the invention, that is to say a steviol, a steviol glycoside derivative or one of their isomers, are such that they allow the use, within a composition according to the invention, of compounds or active agents which normally cannot be used on account of being difficult to formulate, dissolve, deliver in a controlled fashion or vectorize.

Thus, as indicated above, an extract according to the invention can advantageously be combined with at least one additional active agent chosen from a sweetener, an amino acid, such as, for example, glycine, a peptide, inosine or a derivative of the latter, guanosine or a derivative of the latter, an agonist of extracellular calcium receptors, an agonist of calcium channels, an antiwrinkle active agent, an antiaging active agent, a moisturizing agent, an antioxidant, a photoprotective agent and their mixtures.

Preferably, an additional active agent can be chosen from a sweetener, an amino acid, a peptide, inosine or a derivative of the latter, guanosine or a derivative of the latter, an agonist of extracellular calcium receptors, an agonist of calcium channels and their mixtures.

Preferably, an additional active agent can be chosen from an antiwrinkle active agent, an antiaging active agent, a moisturizing agent, an antioxidant, a photoprotective agent, a sunscreen, in particular a UV screening agent, and their mixtures.

The sweeteners under consideration as additional active agent can be described as secondary sweetener in that they are necessarily distinct from the main active agent according to the present invention. Mention may be made, as secondary sweetener, of those of natural or biotechnology origin, such as saccharide or polysaccharide polyols or aminated molecules, in particular thaumatin or extract of the arils of *Thaumatococcus daniellii* or katemfe, or their analogues, precursors or synthetic or semisynthetic derivatives. Mention may also be made of "high intensity sweeteners", such as xylitol ($C_5$), erythritol ($C_4$), sucralose or neohesperidine dihydrochalcone or NHDC (E959), and "bulk sweeteners", such as sorbitol, maltitol, isomalt, mannitol, lactitol, glycerol and its derivatives, fructose and its derivatives, maltose and its derivatives, sucrose and its derivatives, glucose and its derivatives, or mannose and derivatives, and also simple monosaccharides, in particular those of natural or biotechnology origin. Mention may also be made of saccharin, acesulfame potassium (or acesulfame K) and cyclamate (or sodium cyclamate).

The term "amino acids" is understood to mean, within the meaning of the present invention, in particular glutamate or N-Me-D-aspartate, in particular as described in WO 2009/071277, and also the calcium receptor activators described in WO 2008/139946. They can also be taurine, glutamine, arginine, citrulline, glycine, serine and N-acetylcysteine.

The choice and the content of these additional active agents depend in particular on the administration route under consideration, which falls within the competence of a person skilled in the art.

These additional active agents can be present in a composition according to the invention in a content ranging from 0.001% to 50% by weight, preferably from 0.01% to 10% by weight and more preferably from 0.01% to 5% by weight, with respect to the total weight of the composition in which they are present.

Composition

Advantageously, the active agent according to the invention, namely steviol, steviol glycoside derivative or one of their isomers, as or not as a mixture with other additional active agent(s), can be formulated in a cosmetic or dermatological composition.

Preferably, a composition of the invention is a cosmetic composition.

According to a first alternative embodiment, the main active agent according to the invention is intended for topical administration.

Thus, the compositions comprising the main active agent according to the invention can be in the form of products for caring for the skin or semimucus membranes, such as a protective, treatment or care composition for the face, for the lips, for the hands, for the feet, for the anatomical folds or for the body (for example, day cream, night cream, make-up-removing cream, make-up base, antisun composition, protective or care body milk, aftersun milk, lotion, gel or foam for the care of the skin or scalp, serum, powder, mask, artificial tanning composition, aftershave composition, hair composition, product for the region of the armpits, or hygiene and cleansing product.

According to a second alternative embodiment, the main active agent according to the invention is intended for oral administration.

Thus, the composition of the invention can be provided in any suitable form, particularly in the form of a solution to be taken orally, a drink, a tablet, a capsule, including a hard gelatin capsule, or alternatively a nutritional food or a nutritional supplement.

According to a third alternative embodiment, the main active agent according to the invention is intended for intracutaneous administration, such as intradermal or subcutaneous administration. This administration can, for example, be carried out by means of a device which makes possible intracutaneous injection (syringe, implant or reservoir and microneedles) or alternatively by means of an ultrasound or iontophoresis device, indeed even a light or thermal device. Such an administration can also be carried out by mesotherapy.

The intracutaneous use of a composition of the invention is to be distinguished from a surgical operation and is targeted only at effecting a surface treatment of the skin for aesthetic, protective, repair or comfort purposes. In other words, the intracutaneous administration route in the present invention is manifested only in superficial penetration of the skin and thus does not come within any medical, surgical or therapeutic context.

It is alternatively possible, intracutaneously, to favor administration using a topical patch.

Preferably, a main active agent according to the invention is intended for topical administration, that is to say for administration by application at the surface of the keratinous substance under consideration.

Preferably, a main active agent in accordance with the invention, when it is present in a composition, can be formulated in a physiologically acceptable medium.

Within the meaning of the present invention, the term "physiologically acceptable medium" is intended to denote a medium suitable for the topical, oral or intracutaneous, such as intraepidermal, intradermal or subcutaneous, administration of a composition.

A physiologically acceptable medium is preferably a cosmetically or dermatologically acceptable medium, that is to say a medium which is devoid of unpleasant odor or appearance and which is entirely compatible with the administration route under consideration.

When the composition is intended for topical administration, that is to say for administration by application at the surface of the keratinous substance under consideration, such a medium is considered to be physiologically acceptable when it does not cause stinging, tightness or redness unacceptable to the user.

When the composition is intended for oral administration, such a medium is considered to be physiologically acceptable when it does not cause digestive intolerance.

Furthermore, when the composition is intended for intracutaneous administration, such a medium is considered to be physiologically acceptable when it does not cause a reaction experienced as unpleasant by the user, for example stinging, tightness or redness, indeed even does not cause inflammatory, allergic, edematous or pruritic reactions.

The composition according to the invention can be provided in any pharmaceutical dosage form normally used in the cosmetic and dermatological fields.

It can in particular be in the form of an aqueous solution, aqueous/alcoholic solution or oily solution, which is optionally gelled, of a dispersion of the lotion type, which is optionally a two-phase or three-phase lotion, of an oil-in-water or water-in-oil or multiple emulsion, of an aqueous gel, of a dispersion of oils in an aqueous phase, in particular using spherules, it being possible for these spherules to be polymer particles or, better still, lipid vesicles of ionic and/or nonionic type, or alternatively in the form of a powder, of a serum, of a paste, of a solid cake which can disintegrate by rubbing an applicator or of a soft or rigid stick which can melt on the skin or semimucus membranes. It can have a solid, pasty or more or less fluid liquid consistency.

With regard to the pharmaceutical dosage formulation under consideration, the active agent according to the invention can be formulated with the usual constituents.

Mention may in particular be made, by way of illustration and without implied limitation of these normal components, of water, solvents, volatile or nonvolatile oils, in particular as described in detail below, waxes, in particular as described below, pigments, fillers, surfactants, gelling agents, preservatives, coloring materials, antioxidants, UV screening agents and their mixtures.

Of course, a person skilled in the art will take care to choose the optional additional compound(s) and/or their amount so that the advantageous properties of the main active agent according to the invention are not, or not substantially, detrimentally affected by the envisaged addition and so that the properties of the compositions resulting therefrom are compatible with the administration route favored.

A composition according to the invention can advantageously be provided in the form of an emulsion, obtained in particular by dispersion of an aqueous phase in a fatty phase (W/O) or of a fatty phase in an aqueous phase (O/W), of liquid or semi-liquid consistency of the milk type, or of soft, semi-solid or solid consistency of the cream or gel type, or alternatively of a multiple emulsion (W/O/W or O/W/O). These compositions are prepared according to the usual methods.

Thus, a composition according to the invention can advantageously comprise from 0.1% to 99.9% by weight and preferably from 30% to 95% by weight of water, with respect to the total weight of said composition.

A composition according to the invention can also advantageously comprise at least one fatty phase which is liquid at ambient temperature and atmospheric pressure.

The amount of oily phase present in the compositions according to the invention can range, for example, from 0.01% to 50% by weight and preferably from 0.1% to 30% by weight, with respect to the total weight of the composition.

Mention may be made, as examples of oils which can be used in the composition according to the invention, of hydrocarbon oils of animal origin, hydrocarbon oils of vegetable origin, synthetic esters and ethers, in particular of fatty acids, linear or branched hydrocarbons of mineral or synthetic origin, fatty alcohols and silicone oils and their mixtures.

Other fatty substances which can be present in the oily phase are, for example, waxes and fatty acids comprising from 8 to 30 carbon atoms, such as stearic acid, lauric acid, palmitic acid and oleic acid. These fatty substances can be chosen in a manner varied by a person skilled in the art in order to prepare a composition having the desired properties, for example of consistency or texture.

Likewise, a composition according to the invention can additionally comprise at least one coloring material chosen, for example, from pigments, pearlescent agents, dyes, effect materials and their mixtures.

These coloring materials can be present in a content ranging from 0.01% to 50% by weight and preferably from 0.01% to 30% by weight, with respect to the total weight of the composition.

A composition according to the invention can additionally comprise at least one filler, in particular in a content ranging from 0.01% to 50% by weight and preferably ranging from 0.01% to 30% by weight, with respect to the total weight of the composition. These fillers can be inorganic or organic and their choice comes within the competence of a person skilled in the art.

As indicated above, the administration of the active agent under consideration according to the invention can be carried out via the use of a device adjusted to the method of administration under consideration, that is to say topical, oral or intracutaneous. The choice of such devices, made in particular from the viewpoint of the type of administration route favored, comes within the general knowledge of a person skilled in the art.

In addition to the devices already described above, the following can also be considered from the viewpoint more particularly of an intracutaneous administration:

- devices for direct topical delivery or for delivery by means of a specific applicator, such as, for example, intracutaneous microinjections, or simple or iontophoretic patches;
- electrical, electromagnetic or magnetic devices which make possible a physical stimulation simultaneous with the application of said composition at the application site;
- devices dedicated to contributing heat and/or cold, thus modifying the electrical signals at certain receptors, such as, for example, the Derm-Ice® device; and
- devices dedicated to contributing light, activating or inhibiting certain enzymatic systems.

In the last two alternatives, the device contributes to stimulating the effectiveness of the active agent according to the invention at the administration site under consideration.

Thus, the present invention is also targeted at a kit comprising at least one container containing a composition comprising steviol, a steviol glycoside derivative or one of their isomers and at least one device appropriate for the administration of said composition to an individual, in particular as described above.

The present invention also relates to a cosmetic method for stimulating, restoring or regulating the metabolism of cells of the skin, in particular fibroblasts, comprising at least one stage of administration, to an individual having need thereof, of at least an effective amount of steviol, of a steviol glycoside derivative or of one of their isomers.

The present invention also relates to a cosmetic method for preventing and/or treating signs of aging of the skin, comprising at least one stage of administration, to an individual having need thereof, of at least an effective amount of steviol, of a steviol glycoside derivative or of one of their isomers.

A cosmetic method according to the invention can be carried out daily, for example at the rate of a single administration per day or of an administration split up into two or three times per day, for example once in the morning and once in the evening.

Throughout the description, including the claims, the expression "comprising a" should be understood as being synonymous with "comprising at least one", unless otherwise specified.

The expressions "between . . . and . . . " and "ranging from . . . to . . . " should be understood as meaning limits included, unless otherwise specified.

The examples and figures which follow are presented by way of illustration and without implied limitation of the invention. The percentages are expressed by weight of starting materials. The compounds are, as the case may be, mentioned as chemical names or as CTFA (International Cosmetic Ingredient Dictionary and Handbook) names.

Example 1: Influence of Rebaudioside A on the Contraction of Fibroblasts a) Principle of the Test The principle of this test consists in studying the effect of the test product, namely rebaudioside A, on a dermis equivalent model consisting of a collagen matrix colonized by normal human fibroblasts.

These conditions are intended to mimic in vitro dermal contractile phenomena. Any contraction is represented by a retraction of the collagen gel, thus resulting in a decrease in the total surface area of the dermis equivalent.

The measurement of this surface area makes it possible to evaluate the effects of contraction of the substances brought into contact beforehand with the dermis equivalent.

b) Products Used in the Trial

The active agent tested is a *Stevia* extract comprising 99% of rebaudioside A sold by Blue California under the name Good'n Sweet™.

The collagen used is of type I (commercial solution). It is extracted from hides of young bovines and is stored in an acidic medium at +4° C.; it polymerizes naturally by reheating to 37° C. and by decreasing the degree of acidity. The collagen is dialysed beforehand against successive baths of water+acetic acid.

The dermal fibroblasts were isolated from human skin explants and cultured in DMEM medium supplemented with: 10% FCS, 2 mM L-glutamine, 50 U/ml penicillin, 50 µg/ml streptomycin. They were used at the $8^{th}$ passage.

c) Protocol

Several series of attached dermis equivalents comprising normal human fibroblasts are prepared: a control series without any treatment and series treated with the test compound for each of the following concentrations: 0.001 and 0.01 mg/ml.

The dermis equivalents are prepared as described in Asselineau et al., Exp. Cell. Res., 1985, 159, 536-539; Models in Dermatology, 1987, vol. 3, pp 1-7, in the following proportions:

| | |
|---|---|
| MEM medium (2X), with or without guanosine: | 45% |
| Fetal Calf Serum: | 10% |
| NaOH (0.1N) | 5% |
| MEM medium (1X): | 4% |
| Collagen: | 26% |
| Fibroblasts: | 10% |

The protocol is as follows for each dermis equivalent: the MEM media are successively introduced, in the presence of additives (1% glutamine, 1% nonessential amino acids, 1% sodium pyruvate, 1% fungizone and 1% penicillin/streptomycin), fetal calf serum and sodium hydroxide NaOH, into a 50 ml centrifuge tube stored in crushed ice. The fibroblasts isolated from human skin explants are then added at the concentration of $1.5 \times 10^5$ cells per 1 ml of culture medium.

A volume/volume mixture of collagen in acetic acid at 1/1000 is then slowly added, against the wall of the tube, so as to observe the appearance of a whitish cloud.

The combined product is then carefully mixed and distributed in the wells of a 12-well culture plate (Costar type, reference 3512) in a proportion of 2 ml of mixture per well.

The final cell concentration is $3 \times 10^4$ cells/dermis equivalent, with a final concentration of collagen of 1 mg/ml.

The culture plate is then placed in an incubator at 37° C. with 5% of $CO_2$.

Once formed after polymerization of the collagen, the dermis equivalents are left adhered to the culture support for 3 days and then detached from the support so that the contraction can begin. These dermis equivalents are taken out of the incubator in order to take images for the purpose of measuring their surface area, this being for each point of the kinetics of contraction (0, 7, 24 and 48 hours after their detachment). They are immediately placed back in the incubator after each measurement point.

The Dermis Equivalents treated (except for the untreated control) with rebaudioside A are treated from D0, the day of their manufacture, by introducing the rebaudioside A at the concentration selected.

Each experimental condition, control and trials with rebaudioside A, was carried out in n=3.

The lattices were subsequently incubated for 7 days with change in the culture medium and photography of the plates on the $1^{st}$ (D1), $3^{rd}$ (D3), $4^{th}$ (D4) and $7^{th}$ (D7) day.

The evaluation of the spontaneous contraction of the treated (with the test compound) and control (without test compound) dermis equivalents is carried out by measuring their surface areas at different times after the beginning of the spontaneous contraction. This method was validated in parallel with a positive control.

The surface areas of the lattices are measured using the NIS-Elements software, basic version 3.10. There corresponds, to this surface area measurement, a percentage of contraction equal to the ratio of the surface areas according to the formula:

% contraction=$(Sp-Si)/Sp \times 100$ where: Sp' represents the surface area of a well of the culture plate; it corresponds to the total surface area of the dermis equivalent before contraction 'Si' represents the surface area of the dermis equivalent at the time i of the kinetics of contraction.

d) Results

The results obtained are described in table I below in terms of percentage of contraction of the treated and untreated Dermis Equivalents at the different times tested. The results are expressed as % with respect to the control.

TABLE 1

| Treatment (in days) | | 1 | 3 | 4 | 7 |
|---|---|---|---|---|---|
| Control (without rebaudioside) | | 100 | 100 | 100 | 100 |
| *Stevia* extract comprising 99% of rebaudioside A (sold by Blue California under the name Good'n sweet ™) | 0.001 mg/ml | 66 | 88 | 86 | 80 |
| | 0.01 mg/ml | 67 | 86 | 89 | 84 | e) Conclusion

The above results testify to the effectiveness of the *Stevia* extract comprising 99% of rebaudioside A (and thus rebaudioside A) on the contraction of the dermis equivalents, with respect to the untreated controls. This effect lasts for up to at least 7 days of culturing, thus demonstrating the effectiveness of rebaudioside in stimulating, restoring or regulating the metabolism of elderly cells of the skin and in preventing and/or treating cutaneous signs of aging.

Example 2: Emulsion Rich in Antiaging Night

| Starting material (INCI name) | % by weight |
|---|---|
| Disodium EDTA | 0.05 |
| Dimethicone/vinyl dimethicone crosslinked polymer | 1.2 |
| Nylon-12 | 5 |
| Sodium styrene copolymer | 0.8 |
| *Stevia* extract comprising 99% of rebaudioside A (sold by Blue California under the name Good'n sweet ™) | 2.0 |
| Octanoylsalicylic acid | 0.5 |
| Octyldodecanol | 2.00 |
| Cyclopentasiloxane | 17.3 |
| Glycerol | 23 |
| Propylene glycol | 6 |
| Dimethicone | 3.8 |
| PEG/PPG-18/18 dimethicone | 2.4 |
| Vegetable oil | 3 |
| Phenyl trimethicone | 4 |
| Silica | 3 |
| Preservatives | 0.9 |
| Water | q.s. for 100 |

Example 3: Overall Antiaging Perfecting Gel

| Starting material (INCI name) | % by weight |
| --- | --- |
| Potassium hydroxide | 1.00 |
| Disodium EDTA | 0.15 |
| Sodium citrate | 0.70 |
| Phenoxyethanol | 0.4 |
| Caprylic/capric triglycerides | 2.00 |
| Xanthan gum | 0.2 |
| Carbomer | 0.3 |
| Polyacrylamide (and) $C_{13}$-$C_{14}$isoparaffin (and) laureth-7 | 2.00 |
| Dimethicone | 1.00 |
| Glycerol | 5.00 |
| Stearic acid | 1.00 |
| Glyceryl stearate (and) PEG-100 stearate | 1.00 |
| *Stevia* extract comprising 99% of rebaudioside A (sold by Blue California under the name Good'n sweet™) | 0.5 |
| Adenosine | 1.00 |
| Salicylic acid | 0.20 |
| Water | q.s. for 100 |

Example 4: Day Care Emulsion

| Starting material (INCI name) | % by weight |
| --- | --- |
| Xanthan gum | 0.4 |
| Potassium hydroxide | 0.3 |
| Dimethicone PEG phosphate | 2 |
| *Stevia* extract comprising 99% of rebaudioside A (sold by Blue California under the name Good'n sweet™) | 0.5 |
| Dicaprylyl carbonate | 2.00 |
| Cyclohexasiloxane | 10 |
| Salicylic acid | 0.5 |
| Ethyl alcohol | 15 |
| Water | q.s. for 100 |
| Carbomer | 0.4 |
| Crosslinked polymer of acrylates/$C_{10}$-$C_{30}$ alkyl acrylate | 0.25 |

Example 5: Intracutaneous Formulation

A solution comprising 0.005% by weight of a *Stevia* extract comprising 99% of rebaudioside A (sold by Blue California under the name Good'n Sweet™) in physiological saline is prepared and the combined mixture is packaged in a sterile bottle.

This solution is provided for injection into the epidermis, alone or as a mixture with vitamin and trace element preparations.

Example 6: Antiaging Care Powder

| Starting material (INCI name) | % by weight |
| --- | --- |
| Mica (and) Titanium Dioxide, sold by Merck under the name Timiron® Super Red 117187 | 0.6 |
| Vinyl Dimethicone/Methicone Silsesquioxane Crosspolymer, sold by Shin-Etsu under the name KSP100 | 8 |
| Tocopherol | 0.2 |
| *Stevia* extract comprising 99% of rebaudioside A, sold by Blue California under the name Good'n sweet™ | 4 |
| Barium Sulfate, sold by Daito Kasei Kogyo Co. Ltd under the name LLD-5 BaSO$_4$(PL) | 3 |
| HDI/Trimethylol Hexyllactone Crosspolymer, sold by Toshiki Pigment under the name Plastic Powder D400 | 15 |
| Acrylates Copolymer, sold by Akzo Nobel under the name Expancel® Microspheres 551 DE 40 d42 | 0.5 |
| Dye | 0.1 |
| Isocetyl Stearate | 1.5 |
| Mica | 8 |
| Dimethicone/Vinyl Dimethicone Crosspolymer, sold by Dow Corning under the name Dow Corning® 9506 Powder | 10 |
| Aluminum Starch Octenylsuccinate (and) Acrylates Copolymer (and) Magnesium Carbonate, sold by Akzo Nobel under the name Natrasorb® HFB | 15 |
| Talc | q.s. for 100 |

Example 7: Drink for Promoting Antiaging Protection of the Skin

| Starting material | Amount |
| --- | --- |
| Grape juice | 5 ml |
| Watermelon juice | 2.5 ml |
| Tomato concentrate, assaying 10% of lycopene | 80 mg |
| Taurine | 150 mg |
| *Stevia* extract comprising 99% of rebaudioside A (sold by Blue California under the name Good'n sweet™) | 250 mg |
| Arginine | 150 mg |
| Vitamin C | 150 mg |
| Zinc | 5 mg |
| Vitamin B6 | 2 mg |
| Water, q.s. for | 50 ml |
| Vitamin B12 | 2 mg |

The invention claimed is:

1. A cosmetic method for stimulating, restoring or regulating metabolism of a skin cell or a cell of a semimucus membrane, the method comprising administering, by an external topical route, a composition comprising from 0.01% to 30% by weight of a steviol glycoside derivative or of a stereoisomer thereof, to an individual in need thereof, wherein the steviol glycoside derivative is selected from the group consisting of rebaudioside A, rebaudioside B, rebaudioside D, rebaudioside E, rebaudioside F, steviolbioside, and mixtures thereof.

2. The method of claim 1, which reduces and/or treats wrinkles, fine lines or a detrimental change in microrelief.

3. The method of claim 1, which strengthens a mechanical property of skin or a semimucus membrane, and/or which strengthens and/or restores elasticity or firmness of the skin.

4. The method of claim 1, wherein the steviol glycoside derivative or stereoisomer thereof is present in a form of an extract of at least one plant of the *Stevia* genus.

5. The method of claim 4, wherein the extract is obtained from leaves of at least one plant of the *Stevia* genus.

6. The method of claim 4, wherein the extract is obtained from leaves of at least one plant of the species *Stevia rebaudiana*.

7. The method of claim 1, wherein the steviol glycoside derivative is rebaudioside A.

8. The method of claim 1, wherein the composition comprises 0.1% to 10% by weight of steviol glycoside derivative or stereoisomer thereof.

9. The method of claim 1, wherein the composition comprises 0.5% to 5% by weight of steviol glycoside derivative or stereoisomer thereof.

10. A cosmetic method for treating a sign of aging of skin or a semimucus membrane, the method comprising administering, by an external topical route, a composition comprising from 0.01% to 30% by weight of a steviol glycoside derivative or of a stereoisomer thereof, to an individual in need thereof, wherein the steviol glycoside derivative is selected from the group consisting of rebaudioside A, rebaudioside B, rebaudioside D, rebaudioside E, rebaudioside F, steviolbioside, and mixtures thereof.

11. The method of claim 10, which reduces and/or treats wrinkles, fine lines or a detrimental change in microrelief.

12. The method of claim 10, which strengthens a mechanical property of skin or a semimucus membrane, and/or which strengthens and/or restores elasticity or firmness of the skin.

13. The method of claim 10, wherein the steviol glycoside derivative or stereoisomer thereof is present in a form of an extract of at least one plant of the *Stevia* genus.

14. The method of claim 13, wherein the extract is obtained from leaves of at least one plant of the *Stevia* genus.

15. The method of claim 13, wherein the extract is obtained from leaves of at least one plant of the species *Stevia rebaudiana*.

16. The method of claim 10, wherein the steviol glycoside derivative is rebaudioside A.

17. The method of claim 10, wherein the composition comprises 0.1% to 10% by weight of steviol glycoside derivative or stereoisomer thereof.

18. The method of claim 10, wherein the composition comprises 0.5% to 5% by weight of steviol glycoside derivative or stereoisomer thereof.

* * * * *